(12) United States Patent
Karur

(10) Patent No.: US 10,377,812 B2
(45) Date of Patent: Aug. 13, 2019

(54) METHOD FOR EFFICIENT PURIFICATION OF HUMAN SERUM ALBUMIN

(71) Applicant: NAVYA BIOLOGICALS PVT LTD., Hubli (IN)

(72) Inventor: Rajyashri Ramakrishna Karur, Hubli (IN)

(73) Assignee: NAVYA BIOLOGICALS PVT LTD, Hubli (IN)

( * ) Notice: Subject to any disclaimer, the term of this patent is extended or adjusted under 35 U.S.C. 154(b) by 143 days.

(21) Appl. No.: 15/540,632

(22) PCT Filed: Jan. 1, 2016

(86) PCT No.: PCT/IB2016/050001
§ 371 (c)(1),
(2) Date: Jun. 29, 2017

(87) PCT Pub. No.: WO2016/108211
PCT Pub. Date: Jul. 7, 2016

(65) Prior Publication Data
US 2017/0349645 A1 Dec. 7, 2017

(30) Foreign Application Priority Data
Jan. 1, 2015 (IN) .......................... 3228/CHE/2014

(51) Int. Cl.
| | | |
|---|---|---|
| *C07K 14/765* | (2006.01) | |
| *C07K 14/76* | (2006.01) | |
| *C07K 1/36* | (2006.01) | |
| *B01D 15/12* | (2006.01) | |
| *B01D 15/32* | (2006.01) | |
| *B01D 15/36* | (2006.01) | |
| *B01D 15/42* | (2006.01) | |
| *C07K 1/18* | (2006.01) | |
| *C07K 1/34* | (2006.01) | |

(52) U.S. Cl.
CPC .......... *C07K 14/765* (2013.01); *B01D 15/125* (2013.01); *B01D 15/327* (2013.01); *B01D 15/362* (2013.01); *B01D 15/363* (2013.01); *B01D 15/424* (2013.01); *C07K 1/18* (2013.01); *C07K 1/34* (2013.01); *C07K 1/36* (2013.01); *C07K 14/76* (2013.01)

(58) Field of Classification Search
None
See application file for complete search history.

(56) References Cited

U.S. PATENT DOCUMENTS

| | | | |
|---|---|---|---|
| 5,612,196 A | 3/1997 | Becquart et al. | |
| 7,993,877 B2 * | 8/2011 | Van Urk | B01D 15/362 435/69.6 |
| 2003/0204060 A1 | 10/2003 | Van Der Laken et al. | |

FOREIGN PATENT DOCUMENTS

| | | |
|---|---|---|
| CN | 101768206 A | 7/2010 |
| EP | 0 570 916 A2 | 11/1993 |
| EP | 0 650 736 A1 | 5/1995 |
| EP | 0 699 687 A2 | 3/1996 |

OTHER PUBLICATIONS

Hidayat Ullah Khan; The Role of Ion Exchange Chromatography in Purification and Characterization of Molecules; Ion Exchange Technologies; Chapter 14, Published by INTECH, open science, open minds, dx.doi.org/10.5772/52537, pp. 13; Date: Nov. 7, 2012.

* cited by examiner

Primary Examiner — Anand U Desai

(57) ABSTRACT

The present invention describes a simple purification process for recombinant human serum albumin. The process results in highly purified protein with limited number of purification steps. The broth containing human albumin is clarified by centrifugation and microfiltration, diafiltered and captured by cation exchange chromatography by a process that allows 140-230 mg of albumin to be captured per ml of resin. Product related impurities are removed by hydrophobic interaction chromatography, optimized to allow 87-97% recovery in flow through mode. The final series of processes are so combined that there is easy transition from one step to the next with minimal interventions and adjustments. The entire process of purification is completed within two days from harvest to final product. Thus a cost-effective process with improved recovery of protein at each step is developed. The purified human serum albumin is analyzed for purity and shows physicochemical characteristics that are similar to standard albumin.

5 Claims, 9 Drawing Sheets

| Amount Loaded (Albumin/ml Resin) | Resident Time (in mins) |
|---|---|
| 0-80 mg | 5 |
| 80-100 mg | 7 |
| 100-120 mg | 9 |
| 120-230 mg | 15 |

FIGURE 10

| Amount Loaded (Albumin/ml Resin) | Resident Time (in mins) |
|---|---|
| 0-80 mg | 5 |
| 80-100 mg | 7 |
| 100-120 mg | 9 |
| 120-140 mg | 15 |

FIGURE 11

| Process | Buffer Used | Column volumes |
|---|---|---|
| Equilibration | 50mM Sodium acetate pH 4.5 | 5 |
| Loading | rHSA sample+2% 1M Sodium acetate pH 4.5 | |
| Wash 1 | 50mM Sodium acetate pH 4.5 | 3 |
| Wash 2 | 25mM Sodium acetate pH 4.5 + 50mM Ammonium sulphate+2% tween 20 | 3 |
| Wash 3 | 25mM Sodium acetate pH 4.5 | 3 |
| Wash 4 | 25mM Sodium acetate pH 4.5+ 2M Urea | 3 |
| Wash 5 | 25mM Sodium acetate pH 4.5 | 3 |
| Elution | 60mM P.B. pH 5.8+10mM Caprylate | 6 |

FIGURE 12

|  | A350/A280 |
|---|---|
| Load | 0.12 |
| Elution | 0.06 |

FIGURE 13

| HCP | < 100 ppb |
|---|---|
| HCD | Not detected |
| Thiol Ratio | 0.75-0.8 |
| Glycation | < 0.3% |
| Pigment | A350/A280): 0.02-0.015 |
| Aggregates | <3% |
| Degradation product | <2% |

FIGURE 14

METHOD FOR EFFICIENT PURIFICATION OF HUMAN SERUM ALBUMIN

PRIORITY CLAIM

This application claims priority from the provisional application numbered 3228/CHE/2014 filed with Indian Patent Office, Chennai on 1 Jul. 2014 and postdated to 1 Jan. 2015 entitled "Novel method for efficient purification of human serum albumin", the entirety of which is expressly incorporated herein by reference.

PREAMBLE TO THE DESCRIPTION

The following specification particularly describes the invention and the manner in which it is to be performed:

DESCRIPTION OF THE INVENTION

Technical Field of the Invention

The present invention discloses a simple, cost-effective purification process of recombinant human serum albumin from different sources. More particularly, the present invention relates to an improvement of the method that enhances recovery of the protein is each step of purification.

Background of the Invention

Human serum albumin is the most abundant soluble, globular, and unglycosylated monomeric protein in human plasma with a molecular weight of 66,437 to 66,600 Dalton. It contains a single unglycosylated polypeptide chain of 585 amino acids and also contains 17 disulphide bridges and a free thiol group. It acts as a carrier molecule and binds to drugs, pigment, fatty acids, metal ions and to other proteins. It also transports hormones, fatty acids, and other compounds, buffers pH and maintains osmotic pressure. Human serum albumin is used to replace lost fluid and help restore blood volume in trauma, burns and surgery patients.

The market demand for human serum albumin is estimated as more than 500 tons per year worldwide. Currently, commercial production of human serum albumin is primarily based on collected human plasma, which is limited in supply but of high clinical demand.

Recombinant human serum albumin is produced in yeasts including *Pichia*, *Saccharomyces*, *Kluyveromyces*, *Hensenuela*, rice and other organisms. The recombinant protein could be produced by growing transgenic plants in fields or greenhouses or by fermentation from different microorganisms. The protein thus produced needs to be purified through a series of steps to finally attain a degree of purity that is equivalent to or better than plasma albumin. One of the biggest challenges in production of albumin is the degree of purity that is required to be attained. While most recombinant proteins need to be purified such that the final product has <100 ppm of host cell proteins (HCPs), recombinant albumin, which is used in high doses, is required to have <100 ppb (parts per billion) of HCPs in the final product. Thus, a thousand-fold greater purity is required for recombinant albumin as compared to other recombinant bio therapeutics.

Purification of the protein to obtain, in pure form, and to homogeneity, free of: coloring material or pigment, host cell proteins, host cell DNA, polysaccharides, lipids, metal ions, degradation and aggregation products of albumin and glycated albumin. Additionally, the Cys 34 free thiol, which works as a free radical scavenger and is involved in carrying out anti-oxidant functions as well as in carrying drugs and other molecules needs to be maintained in its reduced form.

Since albumin tends to bind to many of the impurities present in the broth the processes developed for purification of this protein are complicated, involving a large number of steps thus increasing the cost while reducing the final recovery of the product.

There are many techniques described for purification of recombinant human serum albumin in patent and non-patent literature. However, these methods involve complicated and multiple steps, which may incur additional cost for the process. The number of steps in prior art results in reduced final recovery contributing to increase in cost of the product.

The Patent Application CN101768206 titled "*Method for purifying recombinant human serum albumin and application thereof*" describes a method for purifying recombinant human serum albumin protein. This method includes the steps of processing the fermented liquid containing recombinant human serum albumin by a ceramic membrane, purifying the supernatant liquid by high salt cation exchange chromatography, hydrophobic layer exchange chromatography and weak anion exchange chromatography. The protein obtained can be used for producing vaccines for humans against viruses with a cell culture method, particularly rabies vaccines. However, the present invention is silent with respect to the purity and the recovery of the protein purified.

The Patent Application EP0570916 A2 titled "*Recombinant human serum albumin, process for producing the same and pharmaceutical preparation containing the same*" describes purification of human serum albumin by sequence of steps including ultra-filtration, heat treatment, acid treatment and another ultra-filtration, followed by subsequent treatments with a cation exchanger, a hydrophobic chromatography carrier and an anion exchanger, and by salting-out such that a pure form of human serum albumin is obtained which does not contain proteinaceous and polysaccharide contaminants and is formulated into a pharmaceutical preparation. This process is efficient to purify recombinant human serum albumin and to provide substantially pure human serum albumin, which does not contain host-related substances and other contaminants and is sufficiently free from coloration. However, the invention involves many steps of purification with final recovery of the product being low.

The Patent Application EP0699687 B1 titled "*Process for purifying recombinant human serum albumin*" describes a process for purifying recombinant human serum albumin by heating a culture medium containing recombinant human serum albumin and the host cells producing this protein, feeding the heated solution upwardly into a fluidized bed in which adsorbent particles are suspended to effect contacting with the adsorbent particles at a pH value of about 3 to 5 and then recovering the adsorbed fraction containing the recombinant protein. The solution is heated in presence of a reducing agent and then subjected to at least one purification treatment selected from a group consisting of hydrophobic interaction chromatography, anion exchanger treatment, chelate resin treatment, boric acid/borate treatment and ultra-filtration. The invention may result in increased purity of the protein.

The Patent Application US20030204060 titled "*Process for the purification of serum albumin*" describes purification of recombinant human serum albumin consisting of a series of steps, optionally by incubation with an anion-exchange adsorbent, followed by affinity chromatography employing a hydrophobic solid phase and using a water-soluble lipid anion as desorbents in the aqueous phase. The immobile phase comprises a carrier coupled to a 2-mercapto or 2-hydroxy alkanoic acid. The protein purified by this method is more than 99.9% pure, particularly more than 99.95% pure.

Thus, there is also a need for developing a process for purification of recombinant human albumin, which results in highly purified protein through minimal steps while optimizing the process to increase the output from each step.

There is also a need for a purification process, which is cost-effective for large scale production of recombinant human serum albumin.

Objectives of the Invention

It is the objective of the present invention to provide a process for purification of recombinant human serum albumin in minimal number of steps.

It is another objective of the present invention to provide a process for purification of recombinant human serum albumin which is cost-effective.

It is yet another objective of the present invention to provide a process for purification of recombinant human serum albumin which results in high purity of the recovered protein.

It is yet another objective of the present invention to optimize the process such that the protein is purified through minimal number steps with increased output from each step.

It is yet another objective of the present invention to optimize the process through a sequence of steps that ensures completion of purification from clarification to bottling in less than two days.

SUMMARY OF THE INVENTION

The present invention discloses a simple, cost-effective purification process for recombinant human serum albumin. The process results in highly purified protein with limited number of purification steps. The present invention also relates to an improvement of the method such that recovery of the protein is increased at each step of purification.

The recombinant human serum albumin produced by fermentation is subjected to purification. The fermentation broth is usually selected from bacteria, fungi, mammalian cells or homogenate of transgenic plant producing recombinant human albumin The cells are separated from the fermentation broth and subjected to centrifugation. The cell free supernatant is microfiltered using 0.1-0.45 micron hollow fiber filters. The microfiltered sample is concentrated and the broth diafiltered against water using hollow fiber filters in a continuous mode till the conductivity is less than 3 mS/cm. The diafiltered sample is loaded on a cation exchange column by online pH adjustment to 4.5 using 2% of 1M Sodium acetate buffer. The eluent from this step is subjected to hydrophobic interaction chromatography, which employs Polypropyleneglycol (PPG), in a flow through mode.

The flow through and wash from purification on HIC is diafiltered and loaded on anion exchange resin for chromatography. The protein thus eluted is concentrated to 200 mg/mi and diafiltered against water. The final concentrated product is brought to 20 mM phosphate buffer, pH 7.0, 1.44 mM sodium chloride and 8 mM sodium caprylate by addition of appropriate volumes of their stock solutions. The protein is sterile filtered and bottled. The bottled protein is subjected to terminal pasteurization at 60° C. for 1-10 hrs.

The final series of process are combined so that there is simple transition from one step to the next, thus reducing the overall time of the process. The entire process of purification is completed within two days from harvest to final product.

The protein purified has a colorless to pale yellow color with a thiol ratio of >0.75, aggregates <2%, physicochemical and binding characteristics of the standard albumin.

The present invention makes the process commercially cost-effective.

BRIEF DESCRIPTION OF THE DRAWINGS

This invention is illustrated in the accompanying drawings.

FIG. 4 also shows the effect of adding caprylate and cysteine on enhanced recovery of the protein in the flow through/wash.

FIG. 10 illustrates the manner of loading of broth after diafiltration on cation exchange column.

FIG. 11 illustrates the manner of loading of broth, after heat treatment, on cation exchange column.

FIG. 12 illustrates the summary of process followed for cation exchange chromatography FIG. 13 illustrates the consistent reduction of pigment at the end of the Cation Exchange chromatography.

FIG. 14 illustrates the specifications of the final purified recombinant human albumin obtained using the described procedure for purification.

DETAILED DESCRIPTION OF THE INVENTION

In order to more clearly and concisely describe and point out the subject matter of the claimed invention, the following definitions are provided for specific terms, which are used in the following written description.

The term "Recombinant human serum albumin" refers to human serum albumin produced by recombinant DNA technology.

The term "Protein purification" refers to a series of processes intended to isolate one or a few proteins from a complex mixture, usually cells, tissues or whole organisms or fermentation broth.

The term "SDS-PAGE" refers to a sodium dodecyl sulfate polyacrylamide gel electrophoresis (SDS-PAGE), a technique for separating proteins based on their ability to move within an electrical current, which is a function of the length of their polypeptide chains or of their molecular weight.

The term "Cation Exchange Chromatography" refers to a form of ion-exchange chromatography that uses resins or packings with functional groups that separates cations. This may include filters with functional groups that separate cations The term "Microfiltration" refers to a physical filtration process where a fluid is passed through a membrane with pore size of 0.1-0.45 microns to separate cells, cell debris, suspended particles or other components which are larger than 0.1-0.45 microns in size, from process liquid.

The present invention discloses a process for purification of recombinant human serum albumin.

Figure 1:
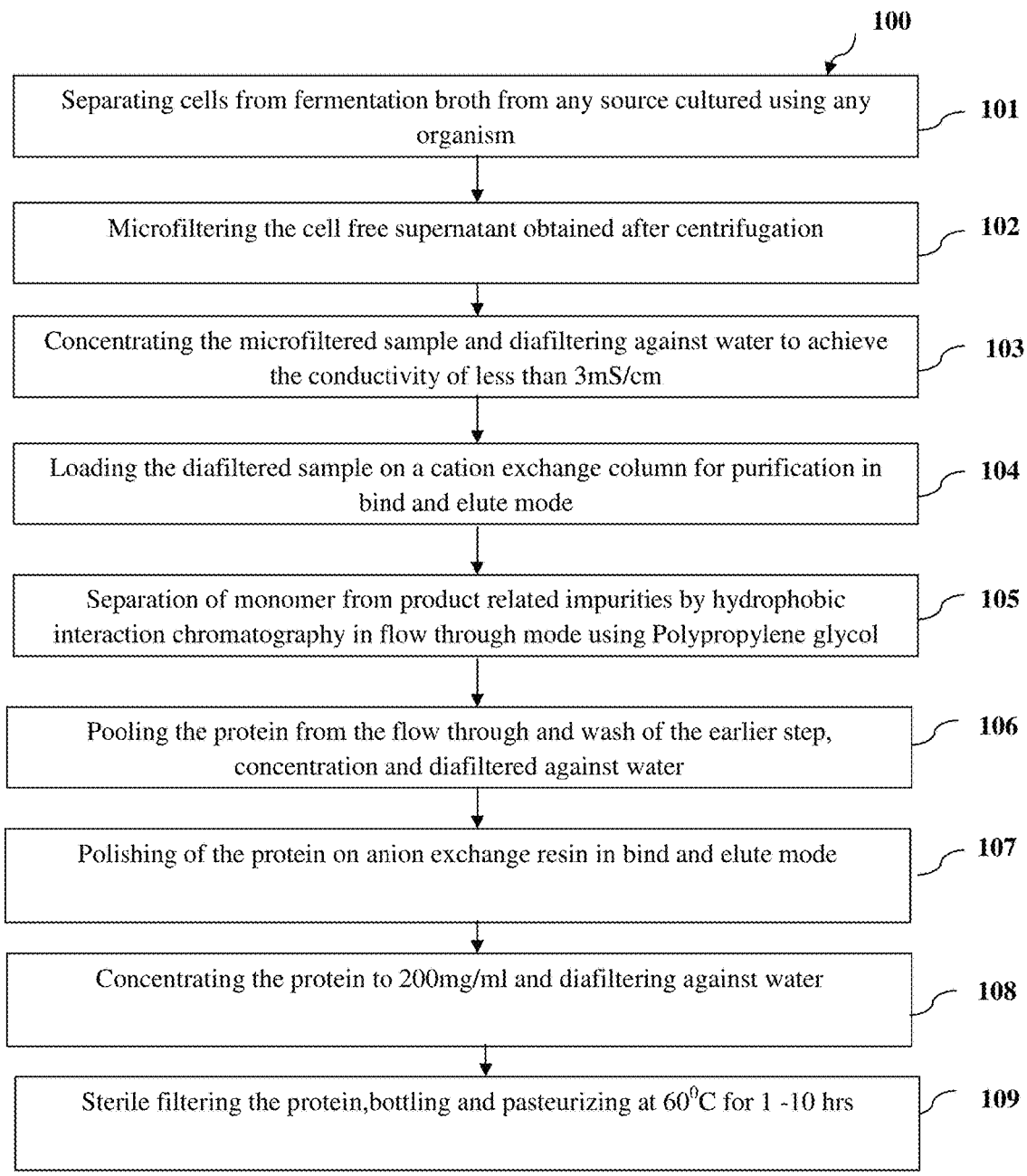
FIG. 1 illustrates a flow chart of a process of purification of recombinant human serum albumin.

FIG. 1 illustrates a flow chart for a process of purification of recombinant human serum albumin. The process (100) of purification starts with (101) separation of cells from fermentation broth from any source cultured using any organism. The fermentation broth is usually selected from the group consisting of bacteria, fungi, mammalian cells or homogenate of transgenic plant producing recombinant human albumin. The broth is diluted with equal volume of water and centrifuged. The protein, can, optionally, be subjected to heat treatment at 60 C for 1-2 hrs for viral inactivation or prevention of acid protease activity before proceeding to the next step of microfiltration. However, this step is optional.

At step (102), the cell free supernatant obtained after centrifugation is subjected to microfiltration using hollow fiber filters. The resultant broth is completely free of particulate matter and cell debris. At step (103), the microfiltered sample is concentrated and diafiltered against water to achieve the conductivity of less than 3 mS/cm. At step (104), the diafiltered sample is purified by cation exchange chromatography. The pH of the sample is adjusted on-line to 4.5 and loaded on cation exchange resin. The resident time of the protein is gradually increased so that a total of 140-230 mg of protein is loaded per ml of the resin. The protein is eluted with 60 mM sodium phosphate, pH 5.8 with 10 mM sodium caprylate. The addition of fatty acids such as caprylate to the elution buffer significantly enhances recovery, reduces aggregation and results in pigment reduction. At step (105), the protein is subjected to hydrophobic interaction chromatography, which employs Polypropylenglycol (PPG), a resin with different selectivity to the other HIC resins, to separate the aggregates and the 45 kDa degradation product from the recombinant human serum albumin. At step (106), the protein pooled from the flow through and wash of the earlier step is concentrated to 50 mg/ml and diafiltered against water. At step (107), the sample pH is adjusted to 7.0 and loaded on anion exchange resin for chromatography. At step (108), the protein is eluted from anion exchange resin with sodium acetate, pH 4.5. The protein eluted is adjusted to pH 7.0 and diafiltered against water. This protein is concentrated to 200 mg/ml and diafiltered against water. Sodium phosphate buffer pH 7.0, sodium chloride and sodium caprylate are added to a final concentration of 20 mM, 144 mM and 8 mM respectively. At step (109), the concentrated protein is sterile filtered and bottled. The bottled protein is subjected to pasteurization at 60° C. for 1-10 hrs.

The final series of process are combined so that there is an easy transition from the last step to the next. This results in reduction of time for completion of the process. The entire process of purification is completed within two days from harvest to final product being obtained. This makes the process cost effective and commercially viable.

Figure 2:
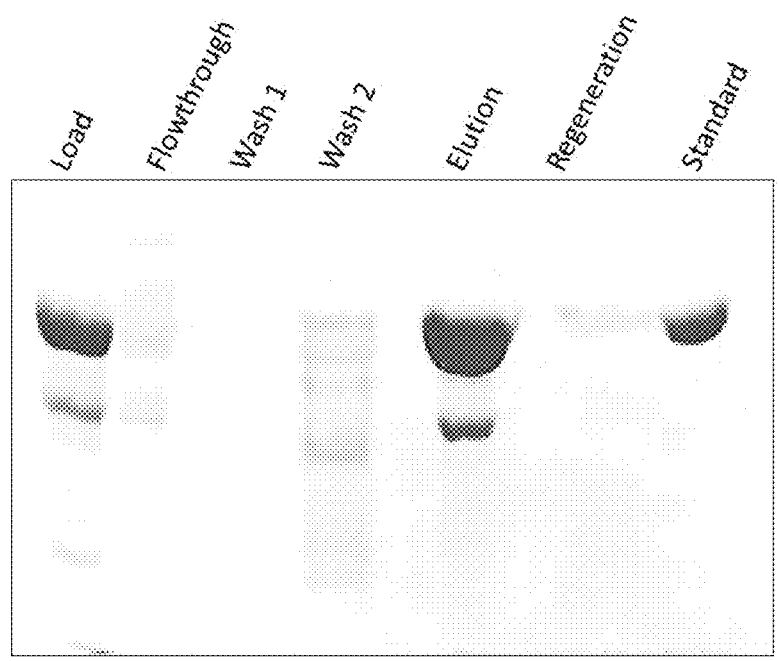
FIG. 2 illustrates the result of SDS PAGE of fractions obtained from cation exchange chromatography loaded on 10% SDS PAGE gel and subjected to coomassie staining.

FIG. 2 illustrates the result of Sodium Dodecyl Sulfate Polyacrylamide Gel Electrophoresis (SDS PAGE) of fractions obtained from cation exchange chromatography loaded on 10% SDS PAGE gel and subjected to coomassie staining. The diafiltered sample is loaded on a cation exchange column by online pH adjustment to 4.5 using 2% of 1M sodium acetate buffer, pH 4.5. The protein is eluted with 60 mM Sodium phosphate, pH 5.8 containing 10 mM Sodium caprylate. The fractions from different steps in the process including flow through, wash 1, wash 2, elution and regeneration are loaded on the gel.

Figure 3:
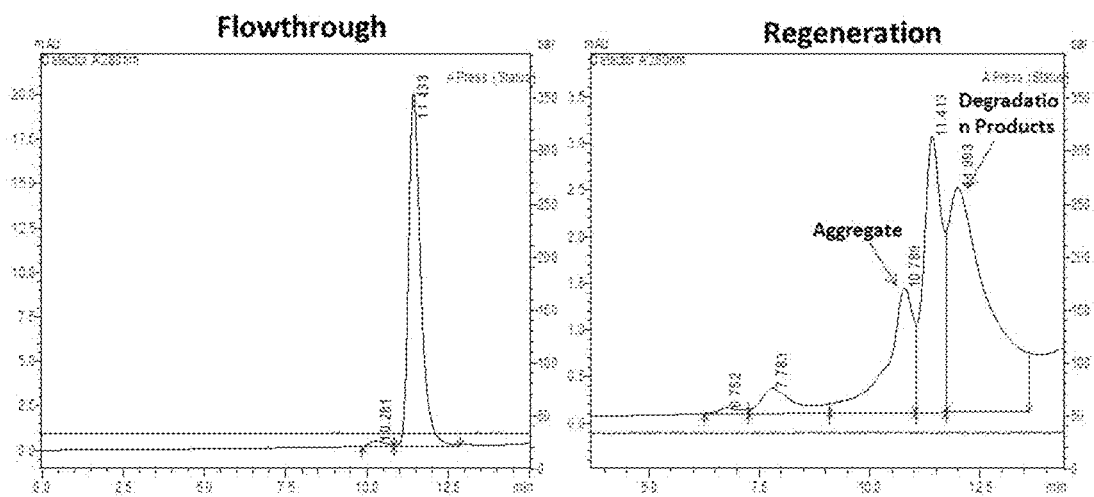
FIG. 3 illustrates the separation of aggregates and degradation products on PPG as seen on SEC-HPLC using BioSep s2000 column.

FIG. 3 illustrates the separation of aggregates and degradation products on PPG, a HIC resin. 50 microliter of the flow through and regeneration samples are injected into BipSep™ s2000 column for Size exclusion chromatography. The results showed the presence of monomeric human serum albumin in the flow through while the regeneration fraction mainly contains aggregates and degradation product.

Figure 4:
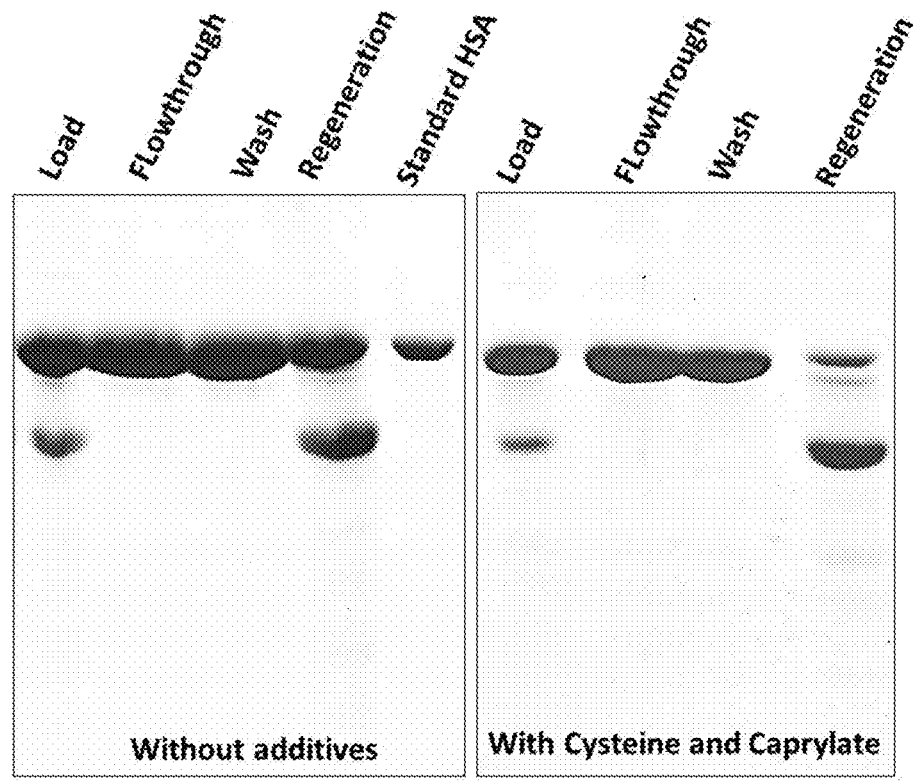
FIG. 4 illustrates the different fractions obtained on fractionation of human serum albumin on PPG loaded on 10% SDS-PAGE Gel.

FIG. 4 illustrates the different fractions obtained on fractionation of human serum albumin on PPG loaded on 10% SDS-PAGE Gel. Left panel illustrates the results of chromatography without addition of caprylate and cysteine to the load while the panel on the right shows the results of addition of caprylate and Cysteine to the load. Addition of caprylate and cysteine results in increasing the amount of monomer in the flow through and wash from 60-70% (without additives) to 87-97%. This process allows the separation of up to 30% aggregates and 30% degradation products in a single step.

Figure 5:
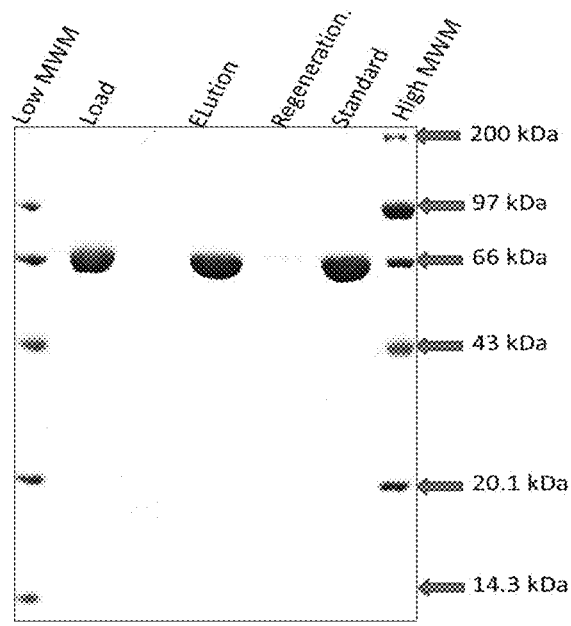
FIG. 5 illustrates the SDS PAGE of the final purified product after Anion exchange chromatography.

FIG. 5 illustrates the SUS PAGE of the final purified product after Anion Exchange chromatography. 20 micrograms of the protein have been loaded on 10% SDS-PAGE and subjected to coomassie blue staining. The results show the purity of the recombinant human serum albumin.

Figure 6:
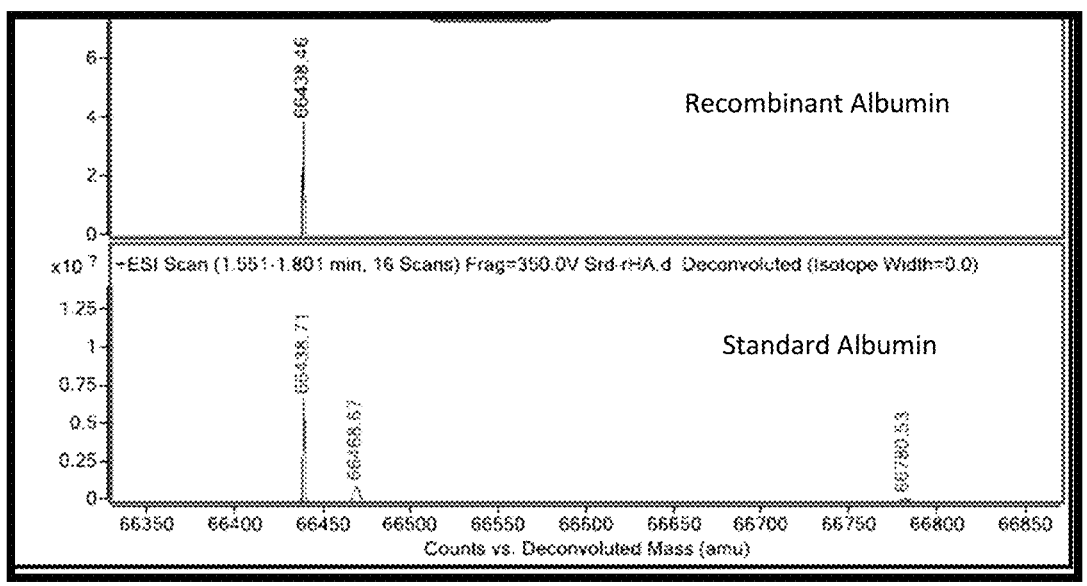
FIG. 6 illustrates the intact mass of the final recombinant human serum albumin compared to standard albumin.

FIG. 6 illustrates the intact mass of the final recombinant human serum albumin. The intact mass of recombinant human serum albumin is 66.483 kDa and is identical to that of standard HSA.

Figure 7:
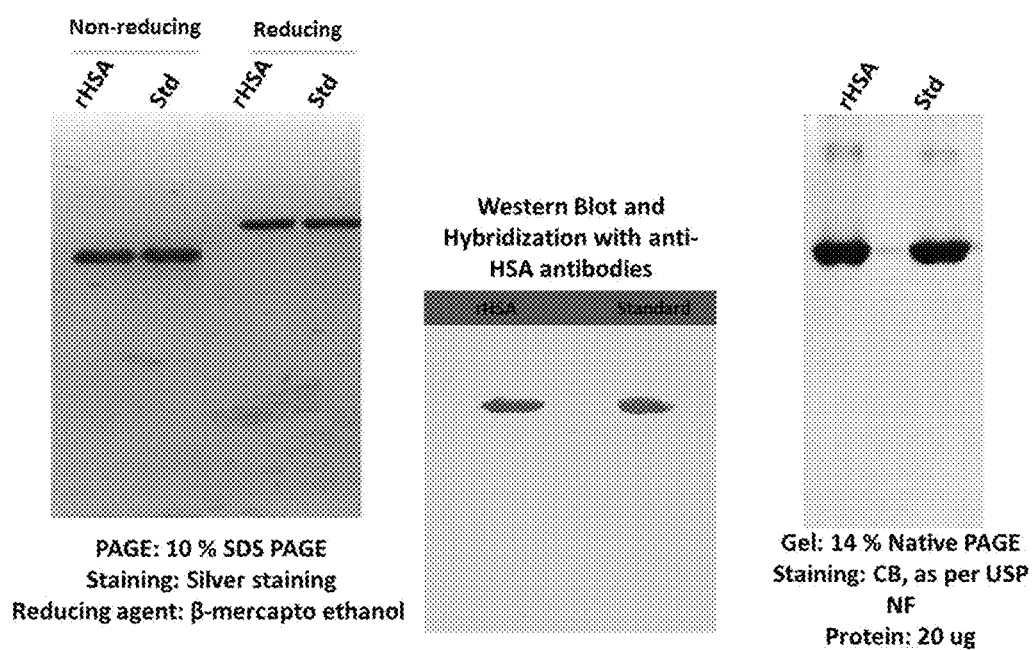
FIG. 7 illustrates Native PAGE, SDS-PAGE under reducing and non-reducing conditions and western blot of recombinant albumin hybridized to anti-human albumin antibody compared to standard albumin.

FIG. 7 illustrates Native PAGE, SUS-PAGE under reducing and non-reducing conditions and western blot and hybridization to anti-human albumin antibody of recombinant albumin compared to standard albumin. The results show identity between the recombinant human serum albumin purified in the present invention to the standard albumin.

Figure 8:
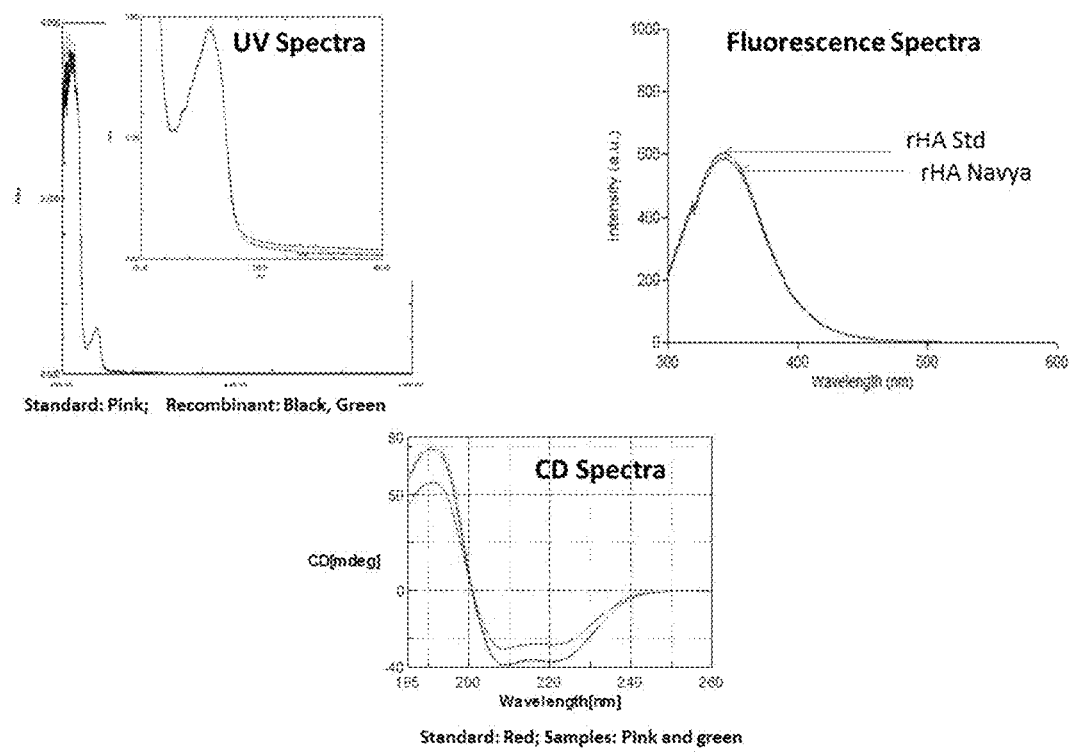
FIG. 8 illustrates the results of comparison of different types of spectra of recombinant human serum albumin with standard albumin.

FIG. 8 illustrates the results of comparison of different types of spectra of recombinant human serum albumin with standard albumin. The purified. recombinant human serum albumin is compared to standard albumin by UV, fluorescence and CD spectroscopy. The results of these spectra showed similarity of recombinant human serum albumin with standard albumin.

Figure 9:
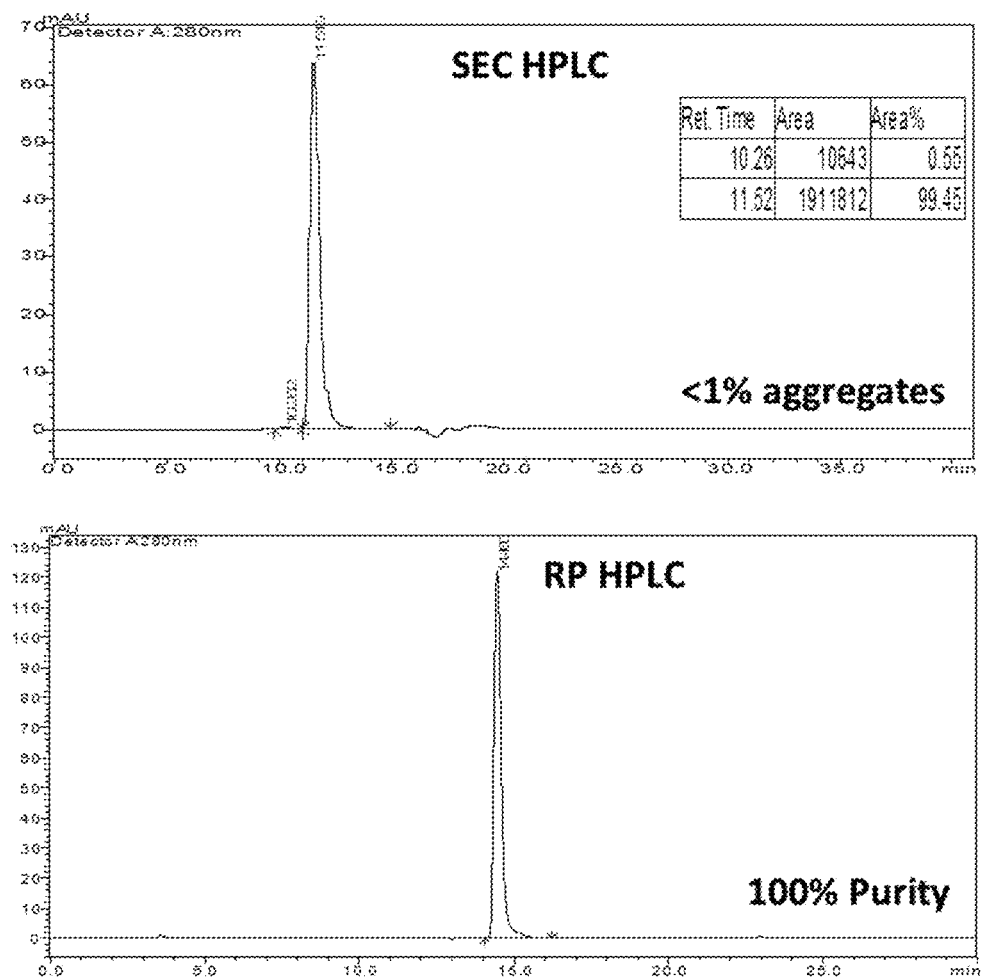
FIG. 9 illustrates the HPLC profiles of the final purified recombinant human serum albumin on SEC-HPLC and RP-HPLC.

FIG. 9 illustrates the HPLC profiles f standard and recombinant albumin. The purified recombinant human serum albumin is subjected to SEC HPLC and RP HPLC. The SEC HPLC showed high percentage of purity of protein with less that 1% of aggregates. The RP HPLC, showed 100% purity of the recombinant human serum.

The recombinant protein thus obtained in the above steps is characterized by mass spectrometry, which showed 100% purity. The N terminal sequencing of the purified recombinant human serum albumin showed identity to plasma albumin. The thiol ratio of the recombinant albumin purified by the above process showed that more than 75% of the molecules have a free thiol group as compared to a maximum of 30% in plasma albumin. Since the free thiol is very important in the function of albumin as a carrier molecule, the recombinant albumin provides a significant advantage over the plasma albumin due to a higher percentage of the molecules comprising free thiol group.

The recombinant human serum albumin shows similar glycation, low-molecular weight impurities, binding characteristics to bilirubin, warfarin and fatty acid as standard albumin.

In order that this invention to be more fully understood the following preparative and testing examples are set forth. These examples are for the purpose of illustration only and are not to be construed as limiting the scope of the invention in any way.

Example 1: Clarification a. The first step of the purification of the protein is cell separation. The fermentation broth is diluted with equal volume of water and subjected to centrifugation at 5000 rpm for 5 minutes. This step results in recovery of >90% of the protein.
b. The cell free supernatant isolated in the previous step is subjected to microfiltration with filters of 0.1-0.45 microns pore size. >90% of protein is recovered with the filtrate being completely free of cells, cell debris and particulate matter.

Example 2: Diafiltration

The microfiltered broth from Example 1 is subjected to diafiltration. The filtrate is concentrated to 20 mg/ml and diafiltered against water using 30 kDa hollow fiber filters till the conductivity is <2 mS/cm. The diafiltered sample is used for column chromatography. The recovery in this step is >90%.

An optional step of heat treatment can be introduced after microfiltration, wherein 5-20 mM sodium caprylate and 5-20 mM cysteine are added to the broth and the samples are heated to 60° C. for 60-120 minutes. This step is effective in denaturation of acid proteases, if any, that would otherwise cause degradation of the protein. However, this step is only optional and not essential to achieve the purification of recombinant albumin.

Example 3: Cation Exchange Chromatography

SP Sepharose FF, a cation exchange resin that is both cheap and has longevity—the resin has been tested for 300 cycles, is packed to a bed height of 15 cm. It is equilibrated with 50 mM sodium acetate buffer, pH 4.5. The diafiltered sample at neutral pH, is diluted with water to 10 mg/ml. The protein is loaded onto the column with on-line pH adjustment to 4.5 using 2% 1M sodium acetate, pH 4.5. The resident time of the protein is gradually increased to obtain maximum binding of albumin to the resin. The loading is performed as shown in FIG. 10.

Under the above conditions, 230 mg of albumin is loaded per ml of the resin. The flow through or equilibration wash does not have any traces of albumin. SP Sepharose FF from GE is claimed to exhibit a binding capacity of 130 mg/ml for BSA at 10% breakthrough, this method of binding enables 75% more binding to the resin thus reducing the cost per gram of the final product.

Further, the samples which are heat treated after diafiltration are diluted to 5 mg/ml with water and loaded onto the column with on-line pH adjustment to 4.5 as shown in FIG. 11.

Under the above conditions, up to 140 mg of albumin is loaded per ml of the resin without any breakthrough. Binding has also been done wherein albumin has been bound up to 80 mg/ml of resin at 5 minutes resident time followed by loading up to 140 mg/ml at 15 minutes resident time. 140 mg albumin/ml of resin is successfully bound under these conditions with no traces of albumin in the flow through The process followed after loading is summarized in FIG. 12.

After loading, the column is washed with equilibration buffer, followed by washing with 3 CVs of 25 mM sodium acetate, pH 4.5 containing 50 mM ammonium sulfate and 2% Tween 20. This step of washing removes pigment, host cell protein and certain degradation products of albumin. This is followed by washing with 2-3 CVs of 25 mM sodium acetate, pH 4.5 followed by 3 CVs of 25 mM sodium acetate, pH 4.5 containing 2M Urea. This step of washing removes pigment very effectively. Urea is removed from the column by washing with 3CVs of 25 mM sodium acetate, pH 4.5.

The protein is eluted with 60 mM sodium phosphate buffer, pH 5.8 with 10 mM sodium caprylate. The protein recovered in this step is >90%.

Other cation exchange resins may also be used in the place of SP Sepharose FF used in this example. Cation exchangers with claims of higher binding capacities will, using the above method of loading, be able to give 75% to two fold higher binding capacity for albumin as compared to the claim by the manufacturer.

The addition of caprylate enhances recovery of the protein and reduces aggregation. Consistent reduction of pigment is seen at the end of the Cation Exchange chromatography as tabulated in FIG. 13.

Example 4: Hydrophobic Interaction Chromatography

The protein purified by Example 3 comprises albumin, its aggregates and its 45 kDa degradation product. The protein is subjected to hydrophobic interaction chromatography in the flow through mode using PPG as the resin of choice.

To the eluent from the previous step, ammonium sulfate is added to a final concentration of 1.2M. Cysteine is added to a final concentration of 10 mM. The pH is adjusted to 7.0 and caprylate concentration readjusted to 10 mM with further addition of desired volume of 1M sodium caprylate. The prepared sample is loaded on the HIC column.

PPG resin is packed to a bed height of 15 cm and equilibrated with 25 mM Phosphate buffer, pH 7.0 with 1.2M ammonium sulfate, 10 mM Cysteine and 10 mM Caprylate. The sample prepared above is loaded on the column at a resident time of 15 minutes. Monomeric albumin does not bind under the above conditions while the 45 kDa degradation product and aggregates of albumin bind to the column. The resin has a binding capacity of 15 mg/ml. Hence up to 150 mg albumin/ml resin is loaded on the column when the sum of aggregates and degradation products of albumin are <10% of the total albumin. If the percentage of aggregates and degradation products of albumin exceeds 10%, the amount of albumin to be loaded is adjusted accordingly.

Most of the monomeric albumin flows out of the column. A wash with 3-5 CVs of equilibration buffer removes the rest of the monomeric albumin, which is loosely bound to the resin. The aggregates and degradation products are eluted with water.

The flow through and wash is pooled together. The recovery in this step is 87-97%. The addition of caprylate results in >87% recovery of monomer while in its absence recovery achieved is <70%. Cysteine helps in keeping the single thiol "free" and reduces the pigment in the final product.

The aggregates at the end of this step are <2.5%, free thiol >70% and A350/A280=0.03-0.035. No traces of degradation products are seen in the final pool.

Example 5: Diafiltration

The flow through and the wash obtained is concentrated to >50 mg/ml and diafiltered against water till conductivity is <2-3 mS/cm. The recovery in this step is 95-98%.

Example 7: Anion Exchange Chromatography

The anion exchange resin (DEAE Sepharose Fast Flow or any other anion exchange resin) is packed to a bed height of 15 cm and equilibrated with 20 mM Phosphate buffer, pH 7.0. The protein obtained in Example 5 is diluted to 5 mg/ml with water and loaded on anion exchange resin. The column is washed with 5 CVs of equilibration buffer followed by elution with 50 mM sodium acetate pH 4.5. This step results in recovery of 98-100% of protein.

The aggregates at the end of this step are <2.5%, free thiol 0.75-0.80. The pigment reduces to A350/A280=0.025-0.015.

Example 8: Concentrating the Protein

The protein eluted from Example 7 is adjusted to pH 7.0 with sodium hydroxide. The protein is concentrated to 200 mg/ml and diafiltered against water. Phosphate buffer, pH 7.0, sodium chloride and sodium caprylate are added to a final concentration of 20 mM sodium phosphate buffer, pH 7.0. 144 mM sodium chloride and 8 mM sodium caprylate respectively. The protein is filtered through 0.2 micron filters into the storage bottles. The bottled protein is subjected to pasteurization at 60° C. for 10 hrs. The final product has the characteristics as shown in FIG. 14.

The physicochemical characteristics of the albumin are identical to the standard albumin as determined by Mass spectrophotometry, N terminal sequencing, C terminal sequencing, IEF, 2 D IEF, UV, Fluorescence and CD spectra and binding characteristic for bilirubin, warfarin and fatty acids.

The protein purified by the process of the present invention results in high purity of recombinant human serum albumin. The entire process of purification is completed within two days from harvest to final product being obtained. This makes the process commercially successful and viable. Hence the process is cost-effective.

I claim:

1. A process for purification of recombinant human albumin, the process comprising the steps of:
   a. separating plurality of cells from fermentation broth or harvest by centrifugation;
   b. microfiltering the obtained cell free supernatant;
   c. concentrating the microfiltered and diafiltering the broth against water;
   d. loading the diafiltered sample on a cation exchange column for purification in bind and elute mode;
   e. separating the monomeric albumin from aggregates and degradation products by hydrophobic interaction chromatography which utilizes polypropylene glycol (PPG) resin in a flow through mode, with 10 mM of cysteine and 10 mM of caprylate wherein recovery of albumin is at least 87%, wherein free thiol ratio is greater than 0.7 and wherein the aggregates are less than 2.5%;
   f. pooling the flow-through and wash and diafiltering the same against water;
   g. loading the albumin on anion exchange resin for chromatography in bind and elute mode;
   h. concentrating the eluted protein and diafiltering against water; and
   i. sterile filtering the protein and subjecting to pasteurization at 60° C. for 1-10 hours.

2. The process as claimed in claim 1, wherein the purity of recombinant human albumin is greater than 97% with reduced pigment and free thiol ratio of greater than 0.75, one or more aggregates less than 2.5% and degradation less than 2% within 60 hrs from harvesting to bottling of recombinant human albumin.

3. The process as claimed in claim 1, wherein fermentation broth is selected from the group consisting of bacteria, fungi, mammalian cells or homogenate of transgenic plant producing recombinant human albumin.

4. The process as claimed in claim 1, wherein loading cation exchange resin by gradual increase in resident time enables increasing the loading capacity by 75-150% above the labelled binding capacity of the resin.

5. The process as claimed in claim 1, wherein Hydrophobic Interaction Chromatography (HIC) in flow through mode further employs addition of one or more fatty acids.

* * * * *